US010004422B2

(12) United States Patent
Alsop et al.

(10) Patent No.: US 10,004,422 B2
(45) Date of Patent: Jun. 26, 2018

(54) METHOD FOR MEASURING MAGNETIZATION TRANSFER BETWEEN MOLECULES WITH MAGNETIC RESONANCE IMAGING

(75) Inventors: David Alsop, Newton, MA (US); Rachel Scheidegger, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1058 days.

(21) Appl. No.: 13/574,876

(22) PCT Filed: Jan. 24, 2011

(86) PCT No.: PCT/US2011/022262
§ 371 (c)(1),
(2), (4) Date: Sep. 20, 2012

(87) PCT Pub. No.: WO2011/091365
PCT Pub. Date: Jul. 28, 2011

(65) Prior Publication Data
US 2013/0190601 A1    Jul. 25, 2013

Related U.S. Application Data

(60) Provisional application No. 61/298,011, filed on Jan. 25, 2010.

(51) Int. Cl.
*A61B 5/055*    (2006.01)
*G01R 33/56*    (2006.01)

(52) U.S. Cl.
CPC .......... *A61B 5/055* (2013.01); *G01R 33/5601* (2013.01); *G01R 33/5605* (2013.01)

(58) Field of Classification Search
CPC combination set(s) only.
See application file for complete search history.

(56) References Cited

U.S. PATENT DOCUMENTS 5,689,186 A    11/1997 Maier et al.
7,400,148 B2    7/2008 Adachi
(Continued)

OTHER PUBLICATIONS

Alsop et al., "inhomogeneous Magnetization Transfer Imaging of Myelin Concentration in Multiple Sclerosis", Proceedings of International Society of Magnetic Resonance in Medicine 15 (2007), p. 2188.*

(Continued)

*Primary Examiner* — Serkan Akar
*Assistant Examiner* — Farshad Negarestan
(74) *Attorney, Agent, or Firm* — Quarles & Brady LLP (57) ABSTRACT

A method for chemical exchange saturation transfer ("CEST") imaging that is more insensitive to off-resonance and magnetization transfer effects than other CEST methods is provided. Sn general, three different images are obtained: one obtained with radio frequency ("RF") saturation about a labeling frequency, one obtained with RF saturation about a reference frequency, and one obtained with RF saturation about both the labeling and reference frequencies. This method, termed saturation with frequency alternating radiofrequency irradiation ("SAFARI"), is also very robust to magnetic field inhomogeneities. The three images, referred to as a labeled image, reference image, and dual frequency image, are selectively combined to produce an image of the subject in which CEST contrast is present, but errors arising from off-resonance and magnetization transfer effects are substantially suppressed.

20 Claims, 4 Drawing Sheets

(56) References Cited

U.S. PATENT DOCUMENTS

| | | | |
|---|---|---|---|
| 2004/0044280 A1 | 3/2004 | Paley et al. | |
| 2007/0282193 A1* | 12/2007 | Brown | A61B 5/0263 600/419 |
| 2008/0197840 A1 | 8/2008 | van Zijl et al. | |
| 2008/0265884 A1* | 10/2008 | Miyazaki | G01R 33/543 324/309 |
| 2010/0016708 A1 | 1/2010 | Katscher et al. | |
| 2014/0062473 A1* | 3/2014 | Miyazaki | G01R 33/50 324/308 |

OTHER PUBLICATIONS

International Search Report as dated Apr. 8, 2011 for International Application No. PCT/US2011/022262.

* cited by examiner

METHOD FOR MEASURING MAGNETIZATION TRANSFER BETWEEN MOLECULES WITH MAGNETIC RESONANCE IMAGING

CROSS-REFERENCE TO RELATED APPLICATIONS

This application represents the U.S. National Stage of International Application No. PCT/US2011/022262, filed Jan. 24, 2011 which claims the benefit of U.S. Provisional Patent Application Ser. No. 61/298,011 filed on Jan. 25, 2010, and entitled "Method for Measuring Magnetization Transfer Between Molecules with Magnetic Resonance Imaging." The foregoing applications are incorporated herein by reference in their-entirety.

STATEMENT REGARDING FEDERALLY SPONSORED RESEARCH

This invention was made with United States government support awarded by the following agency: National Institutes of Health, NIH CA115745 and NIH EB004582. The United States government has certain rights in this invention.

BACKGROUND OF THE INVENTION

The field of the invention is systems and methods for magnetic resonance imaging ("MRI"). More particularly, the invention relates to systems and methods for chemical exchange saturation transfer ("CEST") MRI.

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped," into the x-y plane to produce a net transverse magnetic moment $M_{xy}$. A signal is emitted by the excited nuclei or "spins," after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp," a "Fourier," a "rectilinear," or a "Cartesian" scan. The spin-warp scan technique employs a variable amplitude phase encoding magnetic field gradient pulse prior to the acquisition of MR spin-echo signals to phase encode spatial information in the direction of this gradient. In a two-dimensional implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction. In a typical 2DFT pulse sequence, the magnitude of the phase encoding gradient pulse, $G_y$, is incremented, $\Delta G_y$, in the sequence of measurement cycles, or "views" that are acquired during the scan to produce a set of k-space MR data from which an entire image can be reconstructed.

There are many other k-space sampling patterns used by MRI systems. These include "radial," or "projection reconstruction," scans in which k-space is sampled as a set of radial sampling trajectories extending from the center of k-space. The pulse sequences for a radial scan are characterized by the lack of a phase encoding gradient and the presence of a readout gradient that changes direction from one pulse sequence view to the next. There are also many k-space sampling methods that are closely related to the radial scan and that sample along a curved k-space sampling trajectory rather than the straight line radial trajectory.

An image is reconstructed from the acquired k-space data by transforming the k-space data set to an image space data set. There are many different methods for performing this task and the method used is often determined by the technique used to acquire the k-space data. With a Cartesian grid of k-space data that results from a 2D or 3D spin-warp acquisition, for example, the most common reconstruction method used is an inverse Fourier transformation ("2DFT" or "3DFT") along each of the 2 or 3 axes of the data set. With a radial k-space data set and its variations, the most common reconstruction method includes "regridding" the k-space samples to create a Cartesian grid of k-space samples and then performing a 2DFT or 3DFT on the regridded k-space data set. In the alternative, a radial k-space data set can also be transformed to Radon space by performing a 1DFT of each radial projection view and then transforming the Radon space data set to image space by performing a filtered backprojection.

Measuring the exchange of magnetization between molecules with nuclear magnetic resonance can provide unique information about the chemical and molecular environment of samples or tissues. One type of such exchange measurement is broadly referred to in the field as magnetization transfer. This technique is capable of measuring the exchange of magnetization from spin species that have very short transverse relaxation times ("$T_2$"). Because many different molecules have short $T_2$, this technique is not particularly specific.

A second type of magnetization exchange occurs between water protons and a molecule with long enough $T_2$ that its difference in frequency from water can be observed. Saturation of the magnetization from this molecule will generally decrease the measurable signal from water. This effect is generally referred to in the field as chemical exchange saturation transfer ("CEST"). Two different types of molecules can generate CEST effects: endogenous, or naturally occurring, molecules and exogenous contrast agents. In either instance, the molecules whose chemical exchange with water produces the CEST effect are generally referred to as a so-called "exchangeable protons."

The CEST imaging method offers three advantages over traditional molecular MRI techniques. First, in some cases the molecules of interest within the subject can be directly detected. This feature mitigates the need for administering contrast agents to the subject. Second, the image contrast mechanism can be controlled with the RF pulses produced by the MRI system and, as such, can be turned on and off when desired. This control allows the location of specific molecules of interest to be detected by comparing images having the desired contrast present to those where it has been turned off. Lastly, the CEST imaging method is far more sensitive than traditional molecular MRI techniques, making it able to detect substantially low concentrations of given molecules.

A number of different molecular groups have been suggested for CEST studies. One such group are the amide protons. Amide protons are present in large numbers on peptides and proteins; therefore, amide proton CEST should be reflective of protein concentration in cells. However, other exchangeable protons are also targeted with CEST imaging methods. Exemplary exchangeable protons include those protons contained in hydroxyl and glycogen, as well as paramagnetic molecules in general.

The size of the CEST effect is determined by how quickly the protons exchange their magnetization with water. This exchange rate is believed to be determined by pH, so the CEST effect can also potentially provide information indicative of altered pH levels. Conventional amide proton CEST imaging methods are described, for example, by J. Zhou, et al., in "Using the Amide Proton Signals of Intracellular Proteins and Peptides to Detect pH Effects in MRI," *Nature Medicine,* 2003; 9:1085-1090, and in U.S. Pat. No. 6,943, 033. Imaging using amide proton transfer contrast has a number of potential applications. For example, low pH is indicative of ischemia and could be used in imaging of stroke and other ischemic diseases.

For amide proton CEST, and many other endogenous CEST applications, a major difficulty arises when attempting to avoid other sources of signal change when saturation of the labile proton line is performed. For example, off-resonance saturation can cause direct saturation of the nearby water line, as well as magnetization transfer effects resulting in saturation of broad molecular lines that exchange magnetization with water.

CEST experiments rely on the difference in CEST effect with the frequency of application. One common imaging approach is to compare an image with saturation applied at the frequency of the molecule of interest with another where the saturation is applied on the opposite side of the water frequency, that is applied at the negative of the first frequency. This is successful only if the position of the water line is known exactly and if the magnetization transfer effect is symmetric around the water line. While these situations might be achievable in vitro, neither are present in vivo, thereby resulting in significant errors when utilizing the aforementioned approach. An alternative is to perform CEST studies at many frequencies and fit the signal as a function of frequency to some model. In addition the fact that the appropriate model is typically not known, the long acquisition time needed to acquire images over many frequencies is a disadvantage. Even with the acquisition of many data points, amide proton CEST in normal tissue is very difficult to measure. CEST, and specifically amide proton transfer CEST, is not currently used in diagnostic applications due to the foregoing difficulties with the imaging method.

It would therefore be desirable to provide a method for chemical exchange saturation transfer ("CEST") imaging in which errors resultant from off-resonance and magnetization transfer effects are substantially mitigated, and in which clinically satisfactory imaging times are achieved.

SUMMARY OF THE INVENTION

The present invention overcomes the aforementioned drawbacks by providing a method for chemical exchange saturation transfer ("CEST") imaging in which three images are acquired and selectively combined in order to produce an image influenced by the CEST contrast mechanism in which errors and image artifacts from off-resonance and magnetization transfer effects are substantially mitigated. In general, three images are acquired with such a method: one with radio frequency ("RF") saturation energy applied at a labeling frequency, one with RF saturation energy applied at a reference frequency, and one with RF saturation energy applied at a both the labeling and reference frequencies. Through a selective combination of the three images produced in this manner, the errors in conventional CEST imaging are substantially mitigated and imaging is more accurate and faster than currently existing methods.

It is an aspect of the invention to repeat the data acquisition of the foregoing method a plurality of times and, during each repetition, shifting the labeling and reference frequencies to a different frequency offset. In this manner, a plurality of labeling, reference, and dual frequency image data are acquired, each respective image data associated with the different respective frequencies. These plurality of labeled, reference, and dual frequency image data may then used to characterize a frequency dependence of at least one of the exchangeable proton, a magnetization transfer spectrum, and a water resonance frequency spectrum.

It is another aspect of the invention to provide a method for producing an image of the subject in accordance with the foregoing method, but in which variations of the center frequency of the water resonance frequency spectrum throughout the subject are compensated for. This compensation is also achieved using a plurality of acquired labeling, reference, and dual frequency image data, with each respective image data being associated with different respective frequency offsets as described above.

It is yet another aspect of the invention to provide a method for producing an image of a subject in which unwanted signals are substantially suppressed and signals from a desired exchangeable proton are significantly increased. In such a method, when acquiring the dual frequency image data, the RF energy applied at the labeling frequency is weighted by a first weighting and the RF energy applied at the reference frequency is weighted by a second weighting factor. The selective combination of the labeled, reference, and dual frequency images is then performed using these first and second weightings such that the unwanted signals are substantially suppressed and signals from the exchangeable proton are significantly increased.

It is yet another aspect of the invention to provide a method for determining at least one of an exchange rate and a density, or concentration, of an exchangeable proton using the foregoing method. For example, the foregoing method is repeated a plurality of times and, during each repetition, at least one of the power and the pulsing rate of the applied RF energy is changed while maintaining the same labeling and reference frequencies. In this manner, a plurality of respective labeled, reference, and dual frequency images are produced. These images are indicative of at least one of an exchange rate and density, or concentration, of the exchangeable proton and are, therefore, utilized to determine these parameters of the exchangeable proton.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
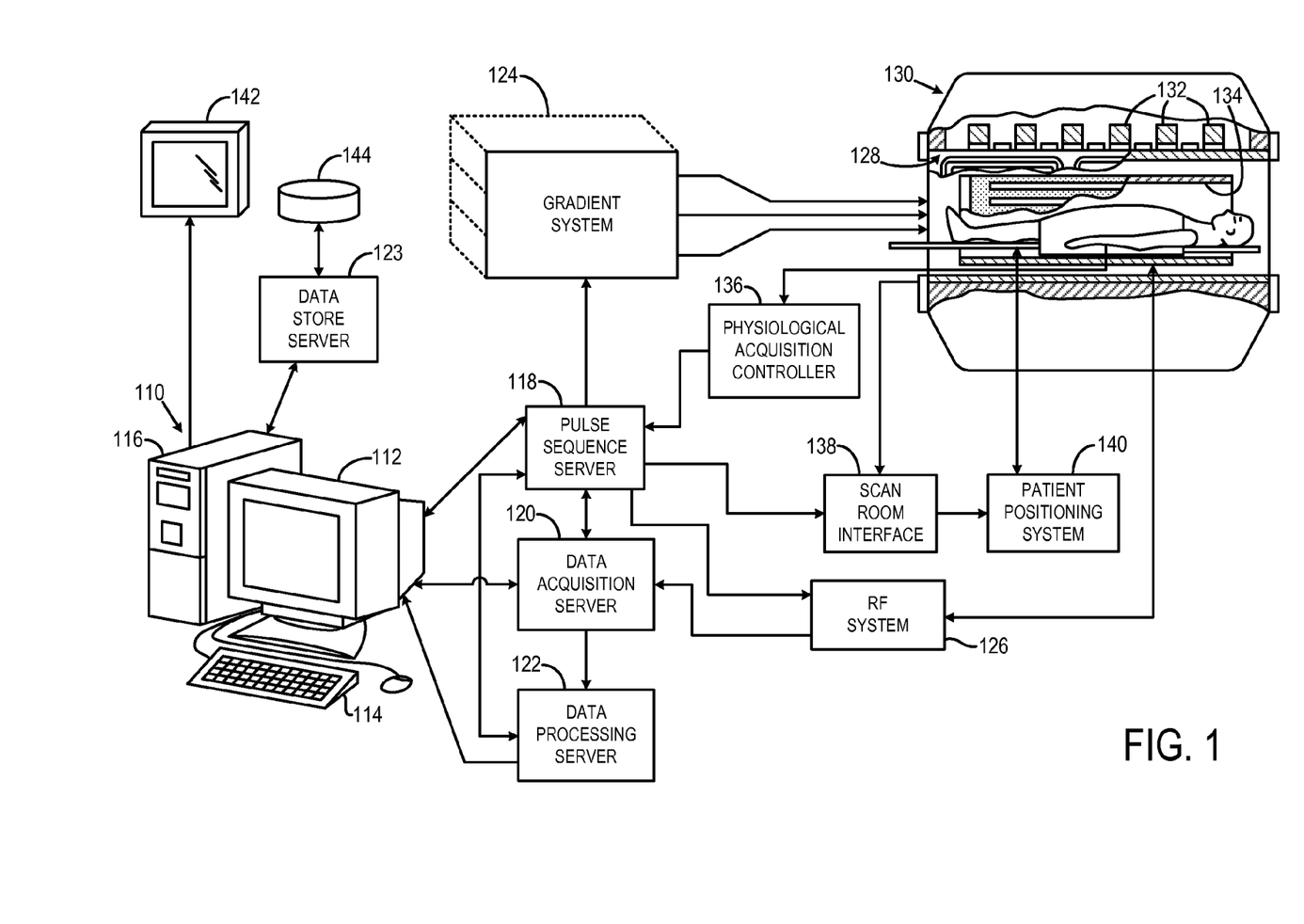
FIG. 1 is a block diagram of an exemplary magnetic resonance imaging ("MRI") system that employs the present invention.

Referring particularly to FIG. 1, the preferred embodiment of the invention is employed in a magnetic resonance imaging ("MRI") system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and a radiofrequency ("RF") system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \tag{1};$$

and the phase of the received MR signal may also be determined:

$$\varphi = \tan^{-1}\left(\frac{Q}{I}\right). \tag{2}$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process MR signals used to detect the arrival of contrast agent in a magnetic resonance angiography (MRA) scan. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a backprojection image reconstruction of acquired MR data; the calculation of functional MR images; and the calculation of motion or flow images.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Described herein is a method for chemical exchange saturation transfer ("CEST") imaging that is more insensitive to frequency shifts and magnetization transfer ("MT") effects than other CEST methods. In general, a three fold subtraction using three different images is performed. This method, termed saturation with frequency alternating radiofrequency irradiation ("SAFARI"), is also very robust to magnetic field inhomogeneities. It will be appreciated by those skilled in the art that the herein described method is applicable not only to amide proton CEST, but also for CEST imaging techniques that utilize other molecular targets, such as glycogen ("glycoCEST"), hydroxyl proton CEST ("OH CEST"), and paramagnetic molecule CEST ("paraCEST"). The term "exchangeable proton" herein refers to those proton or other molecular targets from which magnetization or saturation is desired to transfer to water protons during a CEST imaging scan.

It is well known in the art that the spin state of so-called "exchangeable" protons, such as amide protons, can be utilized to influence the spins state of water protons through exchange processes. The exchangeable protons can be saturated by applying RF energy thereto. Such saturation is also referred to as labeling the exchangeable protons. The saturation of the exchangeable protons is subsequently transferred to the water protons, depending upon the rate of exchange between the two spin populations, and hence is detectable with MRI. It is the transfer of this saturation through chemical exchanges between the exchangeable and water protons that forms the basis of CEST imaging methods.

Figure 2A:
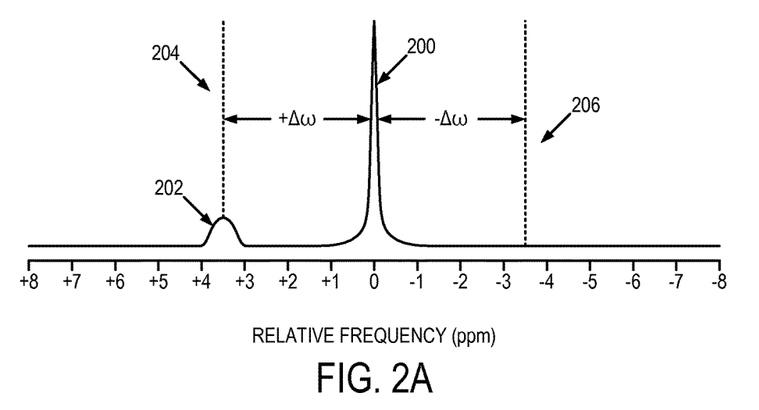
FIG. 2A is a graphic illustration of an exemplary frequency spectrum that includes a water proton resonance peak and an amide proton resonance peak.
Figure 2B:
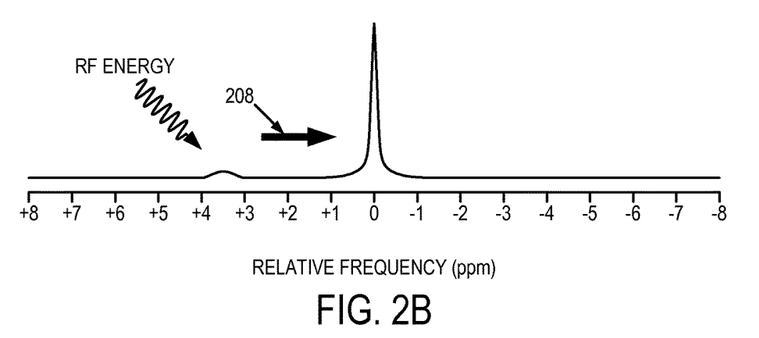
FIG. 2B is a graphic illustration of the effect of the application of radio frequency ("RF") energy at a labeling frequency that is around the resonance frequency of an exchangeable proton, such as an amide proton, on detectable signal from water protons adjacent the exchangeable proton.
Figure 2C:
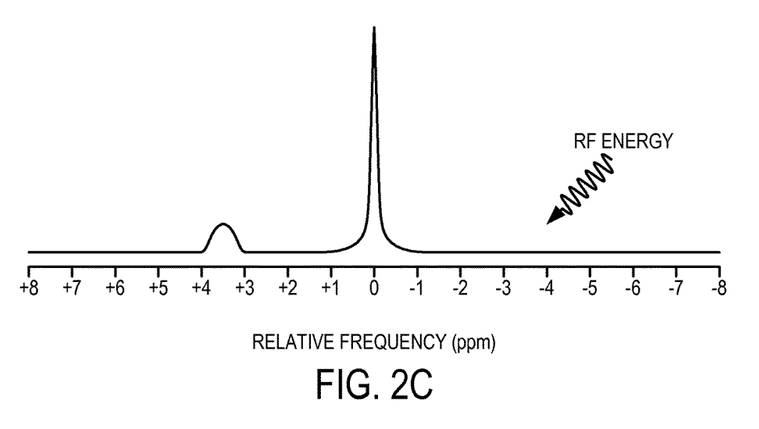
FIG. 2C is a graphic illustration of the effect of the application of RF energy at a reference frequency, equal to the negative of the labeling frequency, on detectable signal from water protons adjacent the exchangeable proton.

Referring now to FIGS. 2A-2C, a graphic illustration of an exemplary method for producing CEST contrast is shown. An exemplary spectrum is illustrated in FIG. 2A, the spectrum including a spectral peak 200 corresponding to water protons and a spectral peak 202 corresponding to amide protons. The amide proton peak 202 exists at a frequency shift relative to the water peak 200. For example, there is a frequency shift of around +3.5 parts per million ("ppm") between the water peak 200 and the amide proton peak 202. Thus, a so-called "labeling spectral line" 204, or "labeling frequency," is centered at or around the resonance frequency of the exchangeable proton, which for an amide proton is shifted about +3.5 ppm relative to the water peak 200. In general, for CEST imaging, the labeling spectral line is selected as a frequency at or around the resonance frequency of the exchangeable proton. A so-called "reference spectral line" 206, or "reference frequency," also exists, and is equal to the negative of the labeling frequency relative to the water peak 200. In the alternative, the labeling and reference frequencies may also be mirrored about the magnetization transfer spectrum.

A first set of image data is acquired with an MRI system by applying RF energy at the labeling spectral line 204, such that the amide proton spins are saturated. In turn, the saturation of the amide protons is transferred through chemical exchange processes to nearby water protons, as indicated by line 208 in FIG. 2B. As a result, the detectable signal from these water protons is reduced. In this manner, a so-called "labeled image data set" is acquired. Referring now to FIG. 2C, a second set of image data is then acquired with the MRI system by applying RF energy at the reference spectral line 206. As this irradiation produces no saturation in the amide proton spins, there is no saturation transferred to the adjacent water spins and, therefore, no resultant decrease in detectable signal. Accordingly, such image data is referred to as "reference image data." An image indicative of the CEST contrast mechanism is thereby produced by subtracting an image reconstructed from the labeled image data set from an image reconstructed from the reference image data set.

In general, saturation effects are highly nonlinear in power. Thus, once saturation of the exchangeable proton line is achieved, a doubling of the power does not substantially increase the saturation. On the other hand, direct off-resonance effects on the water line, and magnetization transfer induced errors, are not saturated and the effects are largely linear in power, especially for relatively small differences in frequency.

Referring again to the method of the present invention, of the three images obtained, one is done so with the RF saturation energy applied equally at two frequencies: a frequency near the exchangeable proton line of interest, and the negative of this frequency, relative to water. As described above, the former is referred to as the labeling frequency and the latter the reference frequency. If the power of the RF saturation energy is sufficient, then the exchangeable proton line is completely saturated. The image obtained in this manner is referred to as the SAFARI, or dual frequency ("DF"), image. Conventional labeling frequency ("LF") and reference frequency ("RF") images are also obtained. It is noted that the power applied during the acquisition of the labeled and reference image data is the same as the power applied during the SAFARI acquisition. However, since the RF energy is equally applied to two different frequencies, the power applied at each frequency during the SAFARI acquisition is one-half the total power applied. It will be appreciated by those skilled in the art, however, that non-equal weightings of RF energy can be applied to the labeling and reference frequencies during the SAFARI acquisition. In such a situation the selective combination of the three images is adjusted in order to minimize unwanted signals and to maximize the signal from the desired exchangeable proton.

Because both the dual frequency and labeling frequency images are obtained with substantially complete saturation of the exchangeable proton, they both represent a signal change, $S_{CEST}$, corresponding to the CEST contrast mechanism. Thus, the following subtraction is performed:

$$S_{CEST}=2 \cdot DF-LF-RF \qquad (3)$$

To the extent that there are asymmetries in magnetization transfer, or a shift in the water line, then if these effects are linear in power, they will cancel. By way of example, an assumption is made that the single frequency irradiation is performed with RF saturation energy power, P, and that the shift of the exchangeable proton line produces a greater effect proportional to power, $P \cdot S_{shift}$, at the labeling frequency. Likewise, the asymmetries of the magnetization transfer produce an error, $P \cdot S_{MT}$. Since the dual frequency SAFARI image has half the power at both the labeling and reference frequencies, the following expression holds:

$$S_{CEST} = \qquad (4)$$
$$2\left(\frac{1}{2} \cdot P \cdot S_{shift} + \frac{1}{2} \cdot P \cdot S_{MT} + S_{CEST}\right) - (S_{CEST} + P \cdot S_{shift} + P \cdot S_{MT}).$$

In contrast, the traditional CEST measurement gives:

$$PF-NF=S_{CEST}+P \cdot S_{MT}+P \cdot S_{shift} \qquad (5)$$

In practice, the herein described SAFARI technique can be implemented with a number of approaches. For example, continuous, two frequency RF irradiation can be employed. This irradiation scheme can readily be achieved via amplitude modulation of a continuous RF wave, such as by cosine modulation, which will produce a sum and difference frequency. In practice, however, continuous irradiation may be difficult to maintain on clinical MRI systems, because pulsed RF amplifiers are often used to reduce the cost for the high power RF systems. Alternatively, CEST can be performed with pulsed RF. Significantly effective saturation is achievable with inversion pulses of between 5-50 ms in duration. Dual frequency saturation is then performed either by alternating the frequency between RF pulses or by using RF pulses with two frequency bands. This latter approach can be achieved by cosine modulating a conventional band selective RF pulse. In general, it is preferable to use phase spoiling to maintain the linear power dependence for direct off-resonance effects of the line. Exemplary methods for phase spoiling are described, for example, in U.S. Pat. No. 4,795,978, and by Y. Zur, et al., in "Spoiling of Transverse Magnetization in Steady-State Sequences," *Magnetic Resonance in Medicine*, 1991; 21:251-263.

Figure 3:
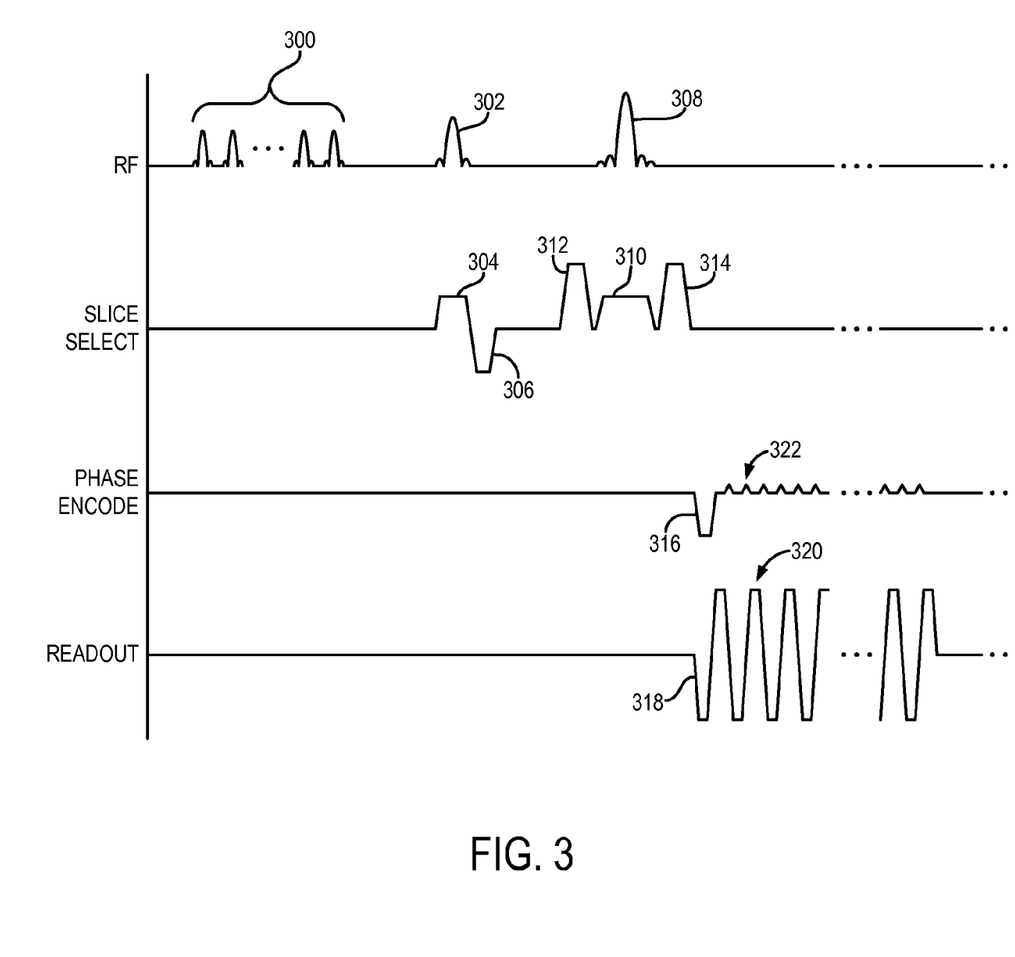
FIG. 3 is a graphic illustration of an exemplary chemical exchange saturation transfer pulse sequence for directing the MRI system of FIG. 1 to acquire image data in accordance with the present invention.

Referring now to FIG. 3, an exemplary pulse sequence employed when practicing the present invention is illustrated. The pulse sequence begins with the application of a saturation radio frequency ("RF") pulse train 300. The saturation pulse train 300 may include a series of RF pulses that are applied at a selected off-resonance frequency in order to "label" the exchangeable proton pool spins, or the saturation pulse train 300 may include a continuous RF wave. As discussed above, the frequency of the RF pulses, or of the continuous RF wave, included in the saturation pulse train 300 is changed depending on the type of image to be obtained. Following the application of the saturation pulse train 300, data acquisition occurs.

By way of example, data acquisition occurs by employing a spin-echo, echo planar imaging ("EPI") method; however, it will be appreciated by those skilled in the art that other methods can be employed to perform data acquisition, such as rapid acquisition with refocused echoes ("RARE") and other fast spin echo ("FSE") based methods. First, an RF excitation pulse 302 is played out in the presence of a slice selective gradient 304. To mitigate signal losses resulting from phase dispersions produced by the slice selective gradient 304, a rephasing lobe 306 is applied after the slice selective gradient 304. Next, a rephasing RF pulse 308 is applied in the presence of another slice selective gradient 310. In order to substantially reduce unwanted phase dispersions, a first crusher gradient 312 bridges the slice selective gradient 310 with a second crusher gradient 314. A pre-phaser gradient waveform 316 is then applied in the phase encoding direction, as is a pre-phaser pulse 318 in the readout direction. Both of the pre-phaser pulses, 316 and 318, are followed by the application of an alternating readout gradient pulse train 320. A spin-echo MR signal is acquired during each positive and negative pulse peak of the readout pulse train 320, and a phase-encoding gradient "blip" 322 is applied between each readout pulse peak to separately phase encode each acquired echo signal. The data acquisition is repeated a plurality of times with a different first slice selective gradient 304 and second slice selective gradient 310 applied during each repetition such that multiple slices of image data are acquired.

Figure 4:
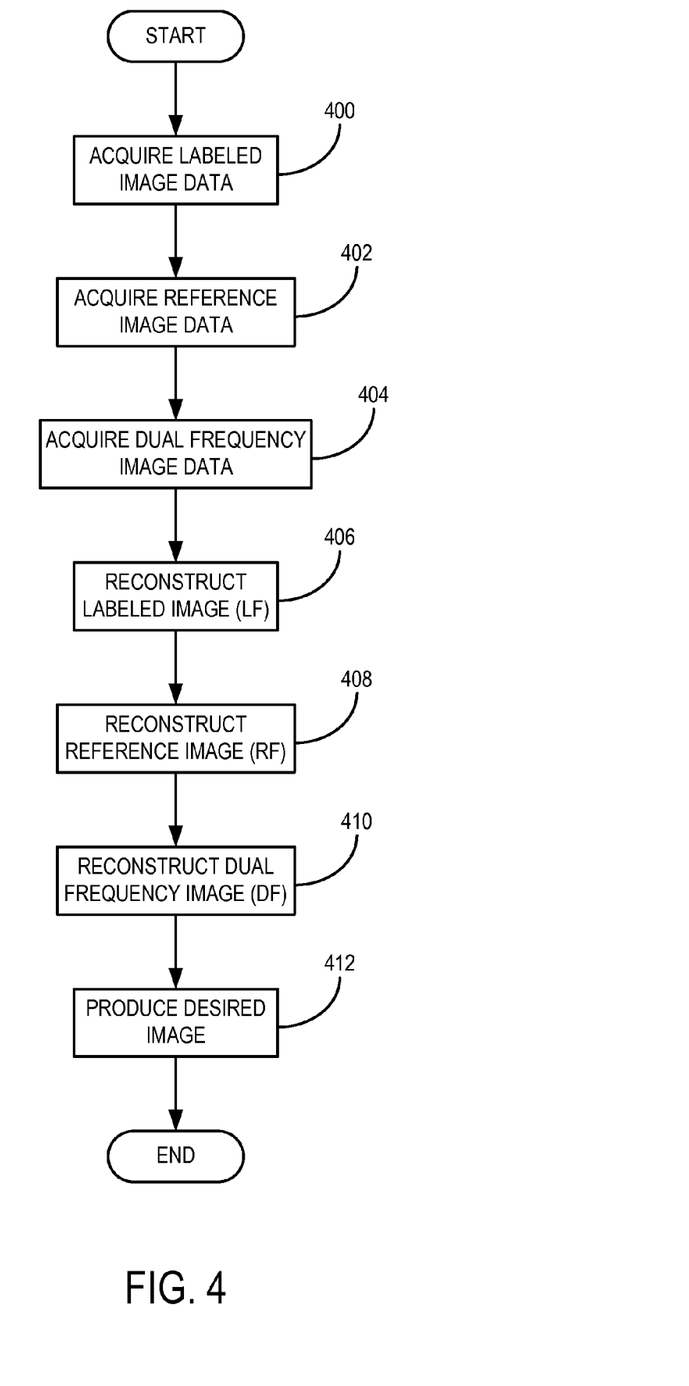
FIG. 4 is a flowchart setting forth the steps of an exemplary method for performing CEST imaging in accordance with the present invention.

Referring now to FIG. 4, a flowchart setting forth the steps of an exemplary method of chemical exchange saturation transfer ("CEST") imaging, which is more insensitive to frequency shifts and magnetization transfer ("MT") effects than other CEST methods, is illustrated. The method begins with the acquisition of three sets of image data. The first set of image data, referred to as the "labeled image data", is acquired, for example, using the pulse sequence illustrated in FIG. 3, as indicated at step 400. For the labeled image data, the frequency of each RF pulse, or the continuous RF wave, in the saturation pulse train 300 is set to a labeling frequency. For example, the labeling frequency is selected as a frequency equal to or around the resonance frequency, relative to water, of the exchangeable proton. Likewise, the second set of image data, referred to as the "reference image data set," is acquired, for example, using the pulse sequence illustrated in FIG. 3, as indicated at step 402. For the reference image data set, the frequency of each RF pulse, or the continuous RF wave, in the saturation pulse train 300 is set to a reference frequency. For example, the reference frequency is selected as the negative of the labeling frequency.

The third set of image data, referred to as the "dual frequency," or SAFARI, image data, is acquired, for example, using the pulse sequence illustrated in FIG. 3, as indicated at step 404. For the dual frequency image data, the frequency of the RF pulses, or the continuous RF wave, in the saturation pulse train 300 alternate between the labeling and reference frequencies employed in steps 400 and 402. For example, the frequency of the odd-numbered RF pulses is selected as the labeling frequency, whereas the frequency of the even-numbered RF pulses is selected as the reference frequency. In the alternative, however, each RF pulse in the saturation pulse train 300 can include two frequency bands: one centered about the labeling frequency and one centered about the reference frequency. By way of example, continuous RF wave saturation at both the reference and labeling frequency can be achieved using amplitude modulation of the continuous RF wave, such as by:

$$B_1(t)=\sqrt{2} \cdot B_1 \sin(\omega t) \qquad (6)$$

where $B_1(t)$ is the continuous RF wave; $B_1$ is the amplitude of the continuous RF wave; $\omega$ is the labeling frequency, for which $-\omega$ is the reference frequency; and t is time. This amplitude modulation generates a frequency response with components at both +ω and −ω.

After the three image data sets described above are acquired, images are reconstructed from the respective data sets. As indicated at step 406, a labeling frequency ("LF") image is reconstructed from the labeled image data. This image reconstruction is a conventional image reconstruction process; however, it will be appreciated by those skilled in the art that any number of image reconstruction methods can be employed without detracting from the present invention. Similarly a reference frequency ("RF") image is reconstructed from the reference image data, as indicated at step 408. Lastly, a dual frequency ("DF"), or SAFARI, image is reconstructed from the dual frequency, or SAFARI, image data, as indicated at step 410. An image depicting substantially only the desired, labeled chemical species containing exchangeable protons is produced by selectively combining the reference, labeled, and dual frequency, or SAFARI, images, as indicated at step 412. For example, the image may be a difference image produced in accordance with Eqn. (3).

In addition to acquiring three image data sets as described above, in some instances it may be advantageous to acquire a second dual frequency image data set, thereby acquiring four total image data sets. By way of example, when pulsed RF energy is used it may be beneficial to acquire a first dual frequency image data set by alternating the frequency of the RF pulses between the labeling frequency (odd pulses) and the reference frequency (even pulses). A second dual frequency image data set may then be acquired by alternating the frequency of the RF pulses between the reference frequency (odd pulses) and the labeling frequency (even pulses). A first and second dual frequency image may then be reconstructed from these first and second dual frequency image data sets, respectively. The first and second dual frequency images may then be averaged together to obtain an average dual frequency image that is selectively combined with the labeled and reference images.

When the RF pulses are alternated between the labeling and reference frequencies, the last RF pulse has to be one or the other. The slight timing difference between the last labeling frequency pulse and the last reference frequency pulse will result in a small, systematic error. Thus, by switching the manner in which the pulses are alternated between the labeling and reference frequencies, and then averaging the two resultant dual frequency images, these small, systematic errors may be mitigated.

The herein described SAFARI method provides for the imaging of exchangeable proton effects that is much more robust to variations in the water frequency caused by non-uniform magnetic fields than prior single reference techniques. However, in some applications, additional correction of water frequency offset effects may be desirable. In these instances, the SAFARI method can be repeated with a different frequency offset being added to the labeling and reference frequencies during each repetition. For example, a frequency offset of +0.5 ppm may be applied to both the labeling and reference frequencies during a given repetition. By varying the frequency offset during each repetition, multiple labeling, reference, and dual frequency image data sets may be obtained, from which a set of multiple labeled, reference, and dual frequency images may be reconstructed. The information contained in these images can be used to correct for water frequency offsets by, for example, interpolating the information contained in each set of the reconstructed images to a larger set of data points and shifting the resulting interpolated data using a fitted z-spectrum water frequency offset for each voxel location in the images. These shifted labeled, reference, and dual frequency images that were acquired using the non-offset labeling and reference frequencies are then selectively combined as described above to arrive at the desired images.

Similar to the technique described, the herein described SAFARI method can be repeated with a different frequency offset being added to the labeling and reference frequencies during each repetition to acquire sets of multiple labeled, reference, and dual frequency images. In this instance, however, the sign of the frequency offset as applied to the labeling frequency is changed before applying to the reference frequency. For example, if a frequency offset of +0.5 ppm is applied to the labeling frequency, then a frequency offset of −0.5 ppm is applied to the reference frequency. Using the sets of multiple images acquired in this manner, the frequency spectrum of the exchangeable protons can be determined. Such a spectrum may contain information about the center frequency of the protons, which may vary with different biochemical contents, and also about the $T_2$ relaxation of the protons. The frequency spectrum can also provide information about the chemical structures containing the exchangeable protons, and may assist quantification of exchange rate and quantification.

The herein described SAFARI acquisition may also be repeated using different RF power levels during each repetition. By way of example, the different power level may be achieved by changing the pulse repetition rate or pulse amplitude when pulsed RF energy is used, or by changing the amplitude of the continuous wave RF energy when continuous wave RF energy is used. By varying the power level in subsequent acquisitions, images with different sensitivity to proton exchange rate and exchangeable proton concentration are obtained. These images may be compared to a family of numerical models to measure the exchange rate and concentration using, for example, a so-called quantifying exchange using saturation power ("QUESP") technique, such as the one described by M. T. McMahon, et al., in "Quantifying Exchange Rates in Chemical Exchange Saturation Transfer Agents Using the Saturation Time and Saturation Power Dependencies of the Magnetization Transfer Effect on the Magnetic Resonance Imaging Signal (QUEST and QUESP): pH Calibration for Poly-L-Lysine and a Starburst Dendrimer," *Magnetic Resonance in Medicine,* 2006; 55:836-847, which is herein incorporated by reference in its entirety. However, contrary to the method described in McMahon, et al., the exchange rate and concentration measurable with the present invention include a reduced sensitivity to magnetization transfer asymmetry and other effects. The images may also be subtracted or otherwise mathematically combined to produce images indicative of either exchangeable proton concentration or exchange rate without the need to calculate measured values.

The present invention has been described in terms of one or more preferred embodiments, and it should be appreciated that many equivalents, alternatives, variations, and modifications, aside from those expressly stated, are possible and within the scope of the invention.

What is claimed is:

1. A method for producing an image of a subject with a magnetic resonance imaging (MRI) system, the steps of the method comprising:
   a) performing, by directing the MRI system, a first saturation pulse sequence in which radio frequency (RF) energy is applied at a labeling frequency of an exchangeable proton, that saturates magnetization corresponding to the exchangeable proton, wherein the labeling frequency of the exchangeable proton is centered at or around the resonance frequency of the exchangeable proton;

b) performing, by directing the MRI system, an image acquisition pulse sequence to acquire labeled image data following step a);

c) performing, by directing the MRI system, a second saturation pulse sequence in which RF energy is applied at a reference frequency;

d) performing, by directing the MRI system, an image acquisition pulse sequence to acquire reference image data following step c);

e) performing, by directing the MRI system, a third saturation pulse sequence in which RF energy is applied at both the labeling frequency and the reference frequency;

f) performing, by directing the MRI system, an image acquisition pulse sequence to acquire dual frequency image data following step e);

g) reconstructing a labeled image from the labeled image data acquired in step b), a reference image from the reference image acquired in step d), and a dual frequency image from the dual frequency image data acquired in step f); and h) producing an image that depicts a chemical exchange saturation transfer (CEST) contrast representative of the exchangeable proton of the subject by selectively combining the labeled image, the reference image, and the dual frequency image thereby reducing errors in the CEST contrast resulting from variations in water resonance frequency caused by spatially inhomogeneous magnetic fields present in the subject.

2. The method as recited in claim 1 in which the RF energy applied in step e) includes a plurality of RF pulses and the frequency of each successive one of the plurality of RF pulses alternates between the labeling frequency and the reference frequency.

3. The method as recited in claim 2 in which step f) is repeated to acquire another dual frequency image data while the order in which the frequency of each successive one of the plurality of RF pulses alternates between the labeling frequency and the reference frequency is reversed; and step g) includes reconstructing another dual frequency image from the another dual frequency image data.

4. The method as recited in claim 3 in which step h) includes averaging the dual frequency image and the another dual frequency image to produce an average dual frequency image that is selectively combined with the labeled image and the reference image.

5. The method as recited in claim 1 in which the RF energy applied in step e) includes a first frequency band centered around the labeling frequency and a second frequency band centered around the reference frequency.

6. The method as recited in claim 1 in which the RF energy applied in step e) is modulated continuous wave RF energy.

7. The method as recited in claim 6 in which the modulated continuous wave RF energy is at least one of amplitude modulated, frequency modulated, and phase modulated.

8. The method as recited in claim 6 in which the modulated continuous wave RF energy is amplitude modulated by a cosine function that is selected so that the amplitude modulated continuous wave RF energy generates a frequency response with components at the labeling frequency and the reference frequency.

9. The method as recited in claim 1 in which the reference frequency is at least one of negative the labeling frequency relative to a water resonance frequency, and negative the labeling frequency relative to the center of a magnetization transfer spectrum of the RF energy applied at the labeling frequency.

10. The method as recited in claim 1 in which steps a)-f) are repeated a plurality of times during which the labeling and reference frequencies are shifted to a different frequency offset during each repetition so that a plurality of labeled, reference, and dual frequency image data are acquired.

11. The method as recited in claim 10 further including characterizing a frequency dependence of at least one of the exchangeable proton, a magnetization transfer spectrum, and a water resonance frequency spectrum using the plurality of labeled, reference, and dual frequency image data.

12. The method as recited in claim 10 further including compensating for variations of a center frequency of a water resonance frequency spectrum resulting from spatially inhomogeneous magnetic fields using the plurality of labeled, reference, and dual frequency image data.

13. The method as recited in claim 1 in which step e) includes weighting the RF energy applied at the labeling frequency by a first weighting and the RF energy applied at the reference frequency by a second weighting factor.

14. The method as recited in claim 13 in which step h) includes selectively combining the labeled, reference, and dual frequency images using the first and second weightings, such that unwanted signals are suppressed and signal from the exchangeable proton is significantly increased.

15. The method as recited in claim 1 in which steps a)-g) are repeated a plurality of times, at least one of a power and a pulsing rate of the RF energy being changed during each repetition, thereby producing a plurality of respective labeled, reference and dual frequency images that are indicative of at least one of an exchange rate and density of the exchangeable proton.

16. The method as recited in claim 1 in which step h) includes subtracting the labeled image and the reference image from two times the dual frequency image.

17. A method for producing an image of a subject with a magnetic resonance imaging (MRI) system, the steps of the method comprising:

a) applying to the subject, with the MRI system, pulsed radio frequency (RF) energy for saturation at a selected labeling frequency of an exchangeable proton, wherein the labeling frequency of the exchangeable proton is centered at or around the resonance frequency of the exchangeable proton;

b) acquiring, with the MRI system, labeled image data from the subject after the application of the pulsed RF energy in step a);

c) applying to the subject, with the MRI system, pulsed RF energy for saturation at a selected reference frequency;

d) acquiring, with the MRI system, reference image data from the subject after the application of the pulsed RF energy in step c);

e) applying to the subject, with the MRI system, pulsed RF energy for saturation at both the selected labeling frequency and the selected reference frequency:

f) acquiring, with the MRI system, dual frequency image data from the subject after the application of the pulsed RF energy in step e);

g) reconstructing a labeled image from the labeled image data acquired in step b), a reference image from the reference image data acquired in step d), and a dual frequency image from the dual frequency image data acquired in step f); and h) producing an image that depicts a chemical exchange saturation transfer (CEST) contrast representative of the exchangeable proton of the subject by selectively combining the labeled image, the reference image, and the dual frequency image thereby reducing errors in the CEST contrast resulting from variations in water resonance frequency caused by spatially inhomogeneous magnetic fields present in the subject.

18. The method as recited in claim 17 in which the pulsed RF energy applied in step e) includes a plurality of RF pulses and the frequency of each successive RF pulse in the pulsed RF energy alternates between the selected labeling frequency and the selected reference frequency.

19. The method as recited in claim 17 in which the pulsed RF energy applied in step e) includes a first frequency band centered around the selected labeling frequency and a second frequency band centered around the selected reference frequency.

20. The method as recited in claim 17 in which the RF energy applied in step e) is a continuous wave that is amplitude modulated using a cosine function that generates a frequency response with components at the labeling frequency and the reference frequency.

\* \* \* \* \*